US006391580B1

(12) United States Patent
Hillman et al.

(10) Patent No.: US 6,391,580 B1
(45) Date of Patent: *May 21, 2002

(54) RAS PROTEINS

(75) Inventors: Jennifer L. Hillman, Mountain View; Y. Tom Tang, San Jose; Preeti Lal, Santa Clara; Karl J. Guegler, Menlo Park; Neil C. Corley; Chandra Patterson, both of Mountain View; Sajeev Batra, Sunnyvale; Mariah R. Baughn, San Leandro, all of CA (US)

(73) Assignee: Incyte Genomics, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/075,454

(22) Filed: May 8, 1998

Related U.S. Application Data

(63) Continuation-in-part of application No. 08/766,551, filed on Dec. 12, 1996, now Pat. No. 5,840,569.

(51) Int. Cl.$^7$ .......................... C12P 21/06; C12Q 1/68; C07H 21/02; C07K 14/00
(52) U.S. Cl. .................... 435/69.1; 435/91.2; 435/91.4; 435/252.3; 435/320.1; 435/6; 536/23.1; 536/23.5; 536/24.31; 530/350
(58) Field of Search .............................. 435/69.1, 91.2, 435/91.4, 252.3, 320.1, 6; 536/23.1, 23.5, 24.31; 530/350

(56) References Cited

PUBLICATIONS

Morimoto et al. (1991) GenBank Database, Accession No. A41636, 1991.*
Morimoto et al. (1991) GenBank Database, Accession No. S72304, 1991.*
Hillier et al. (1996) EST Database, Accession No. AA151425, 1996.*
Barbacid, M., "ras genes", *Annu. Rev. Biochem.* 56: 779–827 (1987).
Treisman, R., "Ternary complex factors: growth factor regulated transcriptional activators", *Curr. Opin. Genet. Dev.*, 4: 96–98 (1994).
Drivas, G.T. et al., "Characterization of Four Novel ras–Like Genes Expressed in a Human Teratocarinoma Cell Line", *Mol. Cell. Biol.* 10: 1793–1798 (1990).
Lee, C.H.J. et al. "Rin, a Neuron–Specific and Calmodulin–Binding Small G–Protein, and Rit Define a Novel Subfamily of Ras Proteins", *J. Neurosci.* 16: 6784–6794 (1996).
Hall, A., "The Cellular Functions of Small GTP–Binding Proteins", *Science*, 249: 635–640 (1990).
Scheffzek, K. et al., "Crystal structure of the nuclear Ras–related protein Ran in its GDP–bound form", *Nature*, 374: 378–381 (1995).
Morimoto, B.H. et al., (Direct Submission), GenBank Sequence Database (Accession S72304), National Center for Biotechnology Information, National Library of Medicine, Bethesda, Maryland, 20894 (GI 240985, GI 240986) Jul. 10, 1992.
Joost, H.G., (Direct Submission), GenBank Sequence Database (Accession X78604), National Center for Biotechnology Information, National Library of Medicine, Bethesda, Maryland, 20894 (GI 1150555, GI 1150556), Aug. 21, 1996.
Wagner, A.C. et al., (Direct Submission), GenBank Sequence Database (Accession U18771), National Center for Biotechnology Information, National Library of Medicine, Bethesda, Maryland, 20894 (GI 619733, GI 619734), Jul. 17, 1995.
Didsbury, J. et al., (Direct Submission), GenBank Sequence Database (Accession M29870, J0538), National Center for Biotechnology Information, National Library of Medicine, Bethesda, Maryland, 20894 (GI 190823, GI 190824) Mar. 15, 1990.
Ren, M. et al., "In its active form, the GRP–binding protein rab8 interacts witha stress–activated protein kinase," *Cell Biol.*, 93: 5151–5155 GenBank database (Accession No. U5095) May 1996.

* cited by examiner

*Primary Examiner*—Karen Cochrane Carlson
*Assistant Examiner*—Rita Mitra
(74) *Attorney, Agent, or Firm*—Incyte Genomics, Inc.

(57) ABSTRACT

The invention provides seven human Ras proteins (RASP) and polynucleotides which identify and encode RASP. The invention also provides expression vectors, host cells, antibodies, agonists, and antagonists. The invention also provides methods for diagnosing, treating or preventing disorders associated with expression of RASP.

9 Claims, No Drawings

RAS PROTEINS

This is a continuation-in-part application of application Ser. No. 08/766,551 filed Dec. 12, 1996, now U.S. Pat. No. 5,840,569 entitled Novel Human GTP-Binding Proteins, the disclosure of which is incorporated herein by reference.

FIELD OF THE INVENTION

This invention relates to nucleic acid and amino acid sequences of seven Ras proteins and to the use of these sequences in the diagnosis, treatment, and prevention of disorders associated with cell proliferation, in particular, cancer and immune disorders.

BACKGROUND OF THE INVENTION

Guanine nucleotide-binding proteins (GTP-binding proteins, or G proteins) participate in a wide range of regulatory functions including metabolism, growth, differentiation, signal transduction, cytoskeletal organization, and intracellular vesicle transport and secretion. These proteins control a diverse sets of regulatory pathways in response to hormones, growth factors, neuromodulators, or other signaling molecules. When these molecules bind to transmembrane receptors, signals are propagated to effector molecules by intracellular signal transducing proteins. Many of these signal transducing proteins are members of GTP-binding proteins.

Low molecular weight (LMW) GTP-binding proteins are small proteins which consist of single polypeptides of 21–30 kDa. These proteins regulate cell growth, cell cycle control, protein secretion, and intracellular vesicle interaction. In particular, the LMW GTP-binding proteins activate cellular proteins by transducing mitogenic signals involved in various cell functions in response to extracellular signals from receptors (Tavitian, A. (1995) C. R. Seances Soc. Biol. Fil. 189:7–12). During this process, the hydrolysis of GTP acts as an energy source as well as an on-off switch for the GTPase activity of the LMW GTP-binding proteins.

The LMW GTP-binding proteins can be classified into at least five subfamilies: Ras, Rho, Ran, Rab, and ADP-ribosylation factor. Despite their sequence variations, all five subfamilies share common conserved structural features. Four sequence regions, termed motifs I–IV, are conserved in the LMW GTP-binding proteins. Motif I is the most variable and has the signature, GXXXXGK. The lysine residue is essential in interacting with the β- and γ-phosphates of GTP. Motif II, III, and IV are highly conserved, with DTAGQE, NKXD, and EXSAX as their respective signatures. These motifs regulate the binding of γ-phosphate, GTP, and the guanine base of GTP, respectively. Most of the membrane-bound LMW GTP-binding proteins generally require a carboxy terminal isoprenyl group for membrane association and biological activity. The isoprenyl group is added post-translationally by a mechanism which recognizes a terminal cysteine residue alone or a terminal cysteine-aliphatic amino acid-aliphatic amino acid-any amino acid (CAAX) motif. Additional membrane-binding energy is often provided by either internal palmitoylation or a carboxy terminal cluster of basic amino acids. The LMW GTP-binding proteins also have a variable effector region, located between motifs I and II, which is characterized as the interaction site for guanine nucleotide exchange factors (GEFs) or GTPase-activating proteins (GAPs). GEFs induce the release of GDP from the active form of the G protein, whereas GAPs interact with the inactive form by stimulating the GTPase activity of the G protein.

The Ras subfamily already indicated supra are essential in transducing signals from receptor tyrosine kinases (RTKs) to a series of serine/threonine kinases which control cell growth and differentiation. Activated Ras genes were initially found in human cancers and subsequent studies confirmed that Ras function is critical in the determination of whether cells continue to grow or become terminally differentiated. Stimulation of cell surface receptors activates Ras which, in turn, activates cytoplasmic kinases. The kinases translocate to the nucleus and activate key transcription factors that control gene expression and protein synthesis. (Barbacid, M. (1987)Ann. Rev Biochem. 56:779–827, Treisman, R. (1994) Curr. Opin. Genet. Dev. 4:96–98.) Mutant Ras proteins, which bind but can not hydrolyze GTP, are permanently activated, and cause continuous cell proliferation or cancer. TC2 1, a Ras-like protein, is found to be highly expressed in a human teratocarcinoma cell line. (Drivas, G. T. et al. (1990) Mol. Cell. Biol. 10: 1793–1798.) Rin and Rit are characterized as membrane-blinding, Ras-like proteins without the lipid-binding CAAX motif and carboxy terminal cysteine. (Lee, C.-H. J. et al. (1996) J. Neurosci. 16: 6784–6794.) Further, Rin is shown to localize in neurons and have calcium-dependant calmodulin-binding activity.

The other members of the LMW GTP-binding proteins have roles in signal transduction that vary with the function of the activated genes and the locations of the GTP-binding proteins that initiate the activity. The Rho GTP-binding proteins control signal transduction pathways that link growth factor receptors to actin polymerization which is necessary for normal cellular growth and division. The Rab proteins control the translocation of vesicles to and from membranes for protein localization, protein processing, and secretion. The ran GTP-binding proteins are located in the nucleus of cells and have a key role in nuclear protein import, the control of DNA synthesis, and cell-cycle progression. (Hall, A. (1990) Science 249:635–640, Scheffzek, K. et al. (1995) Nature 374:378–381.)

The discovery of seven human Ras proteins and the polynucleotides which encode them satisfies a need in the art by providing new compositions which are useful in the diagnosis, treatment, and prevention of disorders associated with cell proliferation, in particular, cancer and immune disorders.

SUMMARY OF THE INVENTION

The invention features substantially purified polypeptides, Ras proteins, referred to collectively as "RASP" and individually as "RASP-1", "RASP-2", "RASP-3", "RASP-4", "RASP-5", "RASP-6", and "RASP-7". In one aspect, the invention provides a substantially purified polypeptide, RASP, comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7.

The invention further provides a substantially purified variant of RASP having at least 90% amino acid identity to the amino acid sequences of SEQ ID NO:1, SEQ ID NO:2, SEQ ID NO:3, SEQ ID NO:4,SEQ ID NO:5, SEQ ID NO:6, or SEQ ID NO:7, or to a fragment of any of these sequences. The invention also provides an isolated and purified polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7. The invention also includes an isolated and purified polynucleotide variant having at least 90% polynucleotide identity to the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7.

Additionally, the invention provides a composition comprising a polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7, as well as an isolated and purified polynucleotide having a sequence which is complementary to the polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7.

The invention also provides an isolated and purified polynucleotide comprising a polynucleotide sequence selected from the group consisting of SEQ ID NO:8, SEQ ID NO:9, SEQ ID NO:10, SEQ ID NO:11, SEQ ID NO:12, SEQ ID NO:13, SEQ ID NO:14, a fragment of SEQ ID NO:8, a fragment of SEQ ID NO:9, a fragment of SEQ ID NO:10, a fragment of SEQ ID NO:11, a fragment of SEQ ID NO:12, a fragment of SEQ ID NO:13, and a fragment of SEQ ID NO:14. The invention further provides an isolated and purified polynucleotide variant having at least 90% polynucleotide identity to the polynucleotide comprising a polynucleotide sequence selected from the group consisting of SEQ ID NO:8, SEQ ID NO:9, SEQ ID NO:10, SEQ ID NO:11, SEQ ID NO:12, SEQ ID NO:13, SEQ ID NO:14, a fragment of SEQ ID NO:8, a fragment of SEQ ID NO:9, a fragment of SEQ ID NO:10, a fragment of SEQ ID NO:11, a fragment of SEQ ID NO:12, a fragment of SEQ ID NO:13, and a fragment of SEQ ID NO:14, as well as an isolated and purified polynucleotide which is complementary to the polynucleotide comprising a polynucleotide sequence selected from the group consisting of SEQ ID NO:8, SEQ ID NO:9, SEQ ID NO:10, SEQ ID NO:11, SEQ ID NO:12, SEQ ID NO:13, SEQ ID NO:14, a fragment of SEQ ID NO:8, a fragment of SEQ ID NO:9, a fragment of SEQ ID NO:10, a fragment of SEQ ID NO:11, a fragment of SEQ ID NO:12, a fragment of SEQ ID NO:13, and a fragment of SEQ ID NO:14.

The invention further provides an expression vector containing at least a fragment of l0 the polynucleotide encoding the polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7. In another aspect, the expression vector is contained within a host cell.

The invention also provides a method for producing a polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7, the method comprising the steps of: (a) culturing the host cell containing an expression vector containing at least a fragment of a polynucleotide encoding RASP under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, SEQ ID NO:3, SEQ ID NO:4, SEQ ID NO:5, SEQ ID NO:6, or SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7 in conjunction with a suitable pharmaceutical carrier.

The invention further includes a purified antibody which binds to a polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7, as well as a purified agonist and a purified antagonist to the polypeptide. The invention also provides a method for treating or preventing a cancer, the method comprising administering to a subject in need of such treatment an effective amount of an antagonist of the polypeptide having an amino acid sequence selected from the group consisting of SEQ ID NO:1, SEQ ID NO:2, SEQ ID NO:3, SEQ ID NO:4; SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7. The invention also provides a method for treating or preventing an immune disorder, the method comprising administering to a subject in need of such treatment an effective amount of an antagonist of the polypeptide having an amino acid sequence selected from the group consisting of SEQ ID NO:1, SEQ ID NO:2, SEQ ID NO:3, SEQ ID NO:4; SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7.

The invention also provides a method for detecting a polynucleotide encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, a fragment of SEQ ID NO:1, a fragment of SEQ ID NO:2, a fragment of SEQ ID NO:3, a fragment of SEQ ID NO:4, a fragment of SEQ ID NO:5, a fragment of SEQ ID NO:6, and a fragment of SEQ ID NO:7 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the nucleic acids of the biological sample are amplified by the polymerase chain reaction prior to the hybridizing step.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"RASP," as used herein, refers to the amino acid sequences of substantially purified RASP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to RASP, increases or prolongs the duration of the effect of RASP. Agonists may include proteins, nucleic acids, carbohydrates, or any other molecules which bind to and modulate the effect of RASP.

An "allelic variant," as this term is used herein, is an alternative form of the gene encoding RASP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding RASP, as described herein, include those sequences with deletions, insertions, or substitutions of different nucleotides, resulting in a polynucleotide the same as RASP or a polypeptide with at least one functional characteristic of RASP. Included within this definition are polymorphisms which may or may not be readily detectable using a particular oligonucleotide probe of the polynucleotide encoding RASP, and improper or unexpected hybridization to allelic variants, with a locus other than the normal chromosomal locus for the polynucleotide sequence encoding RASP. The encoded protein may also be "altered," and may contain deletions, insertions, or substitutions of amino acid residues which produce a silent change and result in a functionally equivalent RASP. Deliberate amino acid substitutions may be made on the basis of similarity in polarity, charge, solubility, hydrophobicity, hydrophilicity, and/or the amphipathic nature of the residues, as long as the biological or immunological activity of RASP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of RASP which are preferably about 5 to about 15 amino acids in length, most preferably 14 amino acids, and which retain some biological activity or immunological activity of RASP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to RASP, decreases the amount or the duration of the effect of the biological or immunological activity of RASP. Antagonists may include proteins, nucleic acids, carbohydrates, antibodies, or any other molecules which decrease the effect of RASP.

As used herein, the term "antibody" refers to intact molecules as well as to fragments thereof, such as Fab, F(ab')$_2$, and Fv fragments, which are capable of binding the epitopic determinant. Antibodies that bind RASP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic RASP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding RASP or fragments of RASP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g., sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using the XL-PCR™ kit (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding RASP, by Northern analysis is indicative of the presence of nucleic acids encoding RASP in a sample, and thereby correlates with expression of the transcript from the polynucleotide encoding RASP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of RASP. For example, modulation may cause an increase or a decrease in protein activity, binding characteristics, or any other biological, functional, or immunological properties of RASP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding RASP, or fragments thereof, or RASP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature.

For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

The term "substantially purified," as used herein, refers to nucleic acid or amino acid sequences that are removed from their natural environment and are isolated or separated, and are at least about 60% free, preferably about 75% free, and most preferably about 90% free from other components with ;which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of RASP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

The Invention

The invention is based on the discovery of new human Ras proteins (RASP), the polynucleotides encoding RASP and the use of these compositions for the diagnosis, treatment, or prevention of cancer and immune disorders. Table 1 shows the sequence identification numbers, Incyte Clone identification number, cDNA library, sequence identifier from National Center for Biotechnology Information (NCBI), and homolog species for each of the human Ras proteins disclosed herein.

TABLE 1

| Protein     | Nucleotide    | Clone ID | Library   | NCBI Homolog | Homolog Source         |
|-------------|---------------|----------|-----------|--------------|------------------------|
| SEQ ID NO:1 | SEQ ID NO:8   | 627565   | KIDNNOT05 | GI 240986    | Mus sp.                |
| SEQ ID NO:2 | SEQ ID NO:9   | 775601   | COLNNOT05 | GI 1150556   | Rattus norvegicus      |
| SEQ ID NO:3 | SEQ ID NO:10  | 1528559  | UCMCL5T01 | GI 619734    | Rattus norvegicus      |
| SEQ ID NO:4 | SEQ ID NO:11  | 1651593  | PROSTUT08 | GI 240986    | Mus sp.                |
| SEQ ID NO:5 | SEQ ID NO:12  | 1673056  | BLADNOT05 | GI 190824    | Homo sapiens           |
| SEQ ID NO:6 | SEQ ID NO:13  | 2703745  | OVARTUT10 | GI 1439642   | Caenorhabditis elegans |
| SEQ ID NO:7 | SEQ ID NO:14  | 3440519  | PENCNOT06 | GI 1656001   | Homo sapiens           |

Nucleic acids encoding the RASP-1 of the present invention is were first identified in Incyte Clone 627265 from a kidney tissue cDNA library (KIDNNOT05) using a computer search for amino acid sequence alignments. A consensus sequence, SEQ ID NO:8, and was derived from the following overlapping and/or extended nucleic acid sequences: Incyte Clones 627265 (KIDNNOT05) and 644359 (BRSTTUT02). SEQ ID NO:8 is a variant of Incyte clone 627051 and of SEQ ID NO:1 of present invention.

In another embodiment, the invention encompasses a polypeptide comprising the amino acid sequence of SEQ ID NO:1. SEQ ID NO:1 is a variant of Incyte Clone 627051 as disclosed in co-pending application Ser. No. 08/766,551 and of SEQ ID NO:4 of present invention. In comparison to SEQ ID NO:3 of the co-pending application, RASP-1 is 90 amino acid residues longer in the amino terminus. In addition, residues 182 and 189 of RASP-1 are Asp and Glu, respectively, rather than Xaa and Gly, respectively, in the corresponding positions as disclosed in SEQ ID NO:3 of the co-pending application. RASP-1 is 259 amino acids in length and has a region encompassing residues 54 to 258 which resembles signature sequences of the GTP-binding Ras superfamily proteins. Residues 53 to 99 and 117 to 134 of RASP-1 resemble the signature sequences of Ran, a small GTP-binding nuclear protein which functions in nucleocytoplasmic transport, RNA synthesis, processing, and export, and cell cycle checkpoint control. Residues 53 to 74, 76 to 92, 94 to 116, 157 to 170, and 194 to 216 resemble transforming protein P21, a GTP-binding Ras proteins whose mutations have been implicated in a number of human tumors. The ATP/GTP-binding site, motif A (P-loop), encompasses residues G59 to T66. RASP1 also has one potential cAMP- and cGMP-dependent protein kinase phosphorylation site at T256; one potential casein kinase II phosphorylation site at S166; two potential protein kinase C phosphorylation sites at S166 and S251; and one potential tyrosine kinase phosphorylation site at Y81. RASP1 has chemical and structural homology with a mouse LMW GTP-binding protein, Rah (GI 240986), a protein important in vesicular trafficking and neuro transmitter secretion. Specifically, RASP1 shares 75% sequence identity with Rah. A fragment of SEQ ID NO:8 from about nucleotide 19 to about nucleotide 80 is useful, for example, as a hybridization probe. Northern analysis shows the expression of this sequence in cardiovascular, musculoskeletal, and reproductive cDNA libraries. Approximately 56% of these libraries are associated with cancer and 18% with inflammation and the immune response.

Nucleic acids encoding the RASP-2 of the present invention were first identified in Incyte Clone 775601 from a sigmoid colon tissue cDNA library (COLNNOT05) using a computer search for amino acid sequence alignments. A consensus sequence, SEQ ID NO:9, was derived from the following overlapping and/or extended nucleic acid sequences: Incyte Clone 775601 (COLNNOT05) and shotgun sequence SAAB00101.

In another embodiment, the invention encompasses a polypeptide comprising the amino acid sequence of SEQ ID NO:2. RASP-2 is 196 amino acids in length and resembles the signature sequences of the GTP-binding Ras superfamily proteins. Residues 32 to 85, 90 to 116, and 167 to 189 resemble the family signatures of ADP-ribosylation factors, a subfamily of LMW GTP-binding Ras proteins involved in protein trafficking. Residues 35 to 58, 63 to 87, and 90 to 115 resemble another GTP-binding Ras protein, SAR1, which mediates vesicular transport between the ER and the Golgi apparatus. The ATP/GTP-binding site, motif A (P-loop), encompasses residues G40 to T47. RASP-2 also has one potential N-glycosylation site at N75; six potential casein kinase II phosphorylation sites at S54, T99, T111, T119, T151, and S163; two potential N-myristoylation sites at G2 and G19; and three potential protein kinase C phosphorylation sites at S89, T111, and S163. RASP-2 has chemical and structural homology with a rat ADP-ribosylation factor-like protein (GI 1150556). Specifically, RASP-2 shares 89% sequence identity with the rat ADP-ribosylation factor-like protein. A fragment of SEQ ID NO:9 from about nucleotide 208 to about nucleotide 270 is useful, for example, as a hybridization probe. Northern analysis shows the expression of this sequence in cardiovascular, hematopoietic and immunological, nervous, and reproductive cDNA libraries. Approximately 33% of these libraries are associated with cancer and 48% with inflammation and immune response.

Nucleic acids encoding the RASP-3 of the present invention were first identified in Incyte Clone 1528559 from a mononuclear cell cDNA library (UCMCL5T01) using a computer search for amino acid sequence alignments. A consensus sequence, SEQ ID NO:10, was derived from the following overlapping and/or extended nucleic acid sequences: Incyte Clone 1528559 (UCMCL5T01) and shotgun sequences SAEA03135, SAEC10396, and SAEC10855.

In one embodiment, the invention encompasses a polypeptide comprising the amino acid sequence of SEQ ID NO:3. RASP-3 is 191 amino acids in length and resembles signature sequences of the GTP-binding Ras superfamily proteins. Residues 63 to 80 and 130 to 168 are similar to two of the family signatures of Ran, a subfamily of Ras proteins which function in nucleocytoplasmic transport, RNA synthesis, processing, and export, and cell cycle checkpoint control. Residues 1 to 19, 22 to 38, 40 to 62, 102 to 115, and 137 to 159 are similar to the family signatures of transforming protein P21, a subfamily of GTP-binding Ras proteins which have been implicated in a number of tumors. The ATP/GTP-binding site, motif A (P-loop), encompasses residues G4 to T11. RASP-3 also has one potential N-glycosylation sites at N82; two potential cAMP- and cGMP-dependent protein kinase phosphorylation sites at S185 and S186; one potential casein kinase II phosphorylation site at S84; one potential N-myristoylation site at G7; and four potential protein kinase C phosphorylation sites at T81, S117, S141, and S180. RASP-3 has chemical and structural homology with a rat Ras protein, Rab26 (GI 619734), which is involved in vesicular transport. Specifically, RASP-3 shares 72% sequence identity with Rab26. A fragment of SEQ ID NO:10 from about nucleotide 92 to about nucleotide 153 is useful, for example, as a hybridization probe. Northern analysis shows the expression of this sequence in hematopoietic and immunological cDNA libraries. All of the cDNA libraries are associated with inflammation and the immune response.

Nucleic acids encoding the RASP-4 of the present invention were first identified in Incyte Clone 1651593 from a prostate tumor tissue cDNA library (PROSTUT08) using a computer search for amino acid sequence alignments. A consensus sequence, SEQ ID NO:11, was derived from the following overlapping and/or extended nucleic acid sequences: Incyte Clones 1651593 (PROSTUT08), 627051 (PGANNOT01), 2954880 (KIDNFET01), 1900926 (BLADTUT06), and 1994547 (BRSTTUT03). SEQ ID NO:11 is a variant of Incyte Clone 627051 as disclosed in co-pending application Ser. No. 08/766,551 and of SEQ ID NO:8 of the present invention.

In one embodiment, the invention encompasses a polypeptide comprising the amino acid sequence of SEQ ID NO:4. SEQ ID NO:4 is a variant of Incyte Clone 627051 in co-pending application Ser. No. 08/766,551 and of SEQ ID NO:1 of the present invention. In comparison to SEQ ID 3 of Incyte Clone 627051 in the co-pending application, RASP-4 is 91 amino acid residues longer in the amino terminus. In addition, residues 183 and 190 of RASP-4 are Asp and Glu, respectively, rather than Xaa and Gly, respectively, as in the corresponding positions of SEQ ID NO:3 of the co-pending application. In comparison to SEQ ID NO:1 of the present invention, RASP-4, SEQ ID NO:4 has an Arg insertion between residues 49 and 50 of SEQ ID NO:1. RASP-4 is 260 amino acids in length and has a region encompassing residues 55 to 259 which resembles signature sequences of the GTP-binding Ras superfamily proteins. Residues 54 to 100 and 118 to 135 are similar to Ran, a subfamily of LMW Ras proteins which function in nucleocytoplasmic transport, RNA synthesis, processing, and export, and cell cycle checkpoint. Residues 54 to 75, 77 to 93, 95 to 117, 158 to 171, and 195 to 217 resemble transforming protein P21, a Ras protein whose mutations have been implicated in a number of tumors. The ATP/GTP-binding site, motif A (P-loop), encompasses residues G60 to T67. RASP-4 also has one potential cAMP- and cGMP-dependent protein kinase phosphorylation site at T257; one potential casein kinase II phosphorylation site at S167; two potential protein kinase C phosphorylation sites at S167 and S252; and one potential tyrosine kinase phosphorylation site at Y82. RASP-4 has chemical and structural homology with a mouse low molecular-weight GTP-binding protein, Rah (GI 240986), a protein important in vesicular trafficking and neurotransmitter secretion. Specifically, RASP-4 shares 75% sequence identity with Rah. A fragment of SEQ ID NO:11 from about nucleotide 15 to about nucleotide 76 is useful, for example, as a hybridization probe. Northern analysis shows the expression of this sequence in cardiovascular, developmental, nervous, and reproductive cDNA libraries. Approximately 55% of these libraries are associated with cancer and 17% with inflammation and the immune response.

Nucleic acids encoding the RASP-5 of the present invention were first identified in Incyte Clone 1673056 from a bladder tissue cDNA library (BLADNOT05) using a computer search for amino acid sequence alignments. A consensus sequence, SEQ ID NO:12, was derived from the following overlapping and/or extended nucleic acid sequences: Incyte Clones 1673056 (BLADNOT05), 936726 (CERVNOT01), 1469924 (PANCTUT02), and 2791380 (COLNTUT16).

In one embodiment, the invention encompasses a polypeptide comprising the amino acid sequence of SEQ ID NO:5. RASP-5 is 190 amino acids in length and has a region encompassing residues 2 to 190 which resembles signature sequences of the GTP-binding Ras superfamily proteins. Residues 84 to 118 are similar to the GTP-binding small nuclear, Ras-associated protein, Ran. Residues 104 to 117 and 152 to 174 resemble another Ras protein, the transforming protein P21. The prenyl group binding site (CAAX box) encompasses residues K187 to L190. RASP-5 also has two potential cAMP- and cGMP-dependent protein kinase phosphorylation sites at T33 and T133; three potential casein kinase II phosphorylation sites at T54, T113, and T165; and three potential protein kinase C phosphorylation sites at S21, T64, and T159. RASP-5 has chemical and structural homology with a human Ras-related C3 botulinum toxin substrate, Rac (GI 190824), a plasma membrane-associated GTP-binding protein implicated in secretory processes in myeloid cells. Specifically, RASP-5 shares about 64% sequence identity with Rac. A fragment of SEQ ID NO:12 from about nucleotide 551 to about nucleotide 612 is useful, for example, as a hybridization probe. Northern analysis shows the expression of this sequence in cardiovascular, developmental, gastrointestinal, hematopoietic and immunological, and reproductive cDNA libraries. Approximately 50% of these libraries are associated with cancer, 21% with inflammation and immune response, and 24% with fetal development and proliferating cell lines.

Nucleic acids encoding the RASP-6 of the present invention were first identified in Incyte Clone 2703745 from a ovarian tumor tissue cDNA library (OVARTUT10) using a computer search for amino acid sequence alignments. A consensus sequence, SEQ ID NO:13, was derived from the following overlapping and/or extended nucleic acid sequences: Incyte Clones 2703745 (OVARTUT10), 495594 (HNT2NOT01), and 873944 (LUNGAST01), and shotgun sequence SBLA02682.

In one embodiment, the invention encompasses a polypeptide comprising the amino acid sequence of SEQ ID NO:6. RASP-6 is 211 amino acid is in length and has a region encompassing residues 14 to 209 which resembles signature sequences of the GTP-binding Ras superfamily proteins. Residues 63 to 114 and 114 to 148 are similar to SAR1, a family of GTP-binding proteins involved in vesicular transport between the ER and the Golgi. Residues 36 to 52, 54 to 76, 116 to 129, and 157 to 179 resemble the family signatures of transforming protein P21, a GTP-binding Ras protein whose mutations have been implicated in a number of tumors. RASP-6 also has two potential N-glycosylation sites at N40 and N193; two potential casein kinase II phosphorylation sites at S161 and T183; two potential cAMP- and cGMP-dependent protein kinase phosphorylation sites at T13 and T183; and four potential protein kinase C phosphorylation sites at S29, S161, T183, and S199. RASP-6 has chemical and structural homology with a C. elegans Ras-related protein (GI 1439642). Specifically, RASP-6 shares about 39% sequence identity with the Ras-related protein. A fragment of SEQ ID NO:13 from about nucleotide 29 to about nucleotide 90 is useful, for example, as a hybridization probe. Northern analysis shows the expression of this sequence in gastrointestinal and reproductive cDNA libraries. Approximately 33% of these libraries are associated with cancer and 33% with fetal development and proliferating cell lines.

Nucleic acids encoding the RASP-7 of the present invention were first identified in Incyte Clone 3440519 from a corpora cavernosa tissue cDNA library (PENCNOT06) using a computer search for amino acid sequence alignments. A consensus sequence, SEQ ID NO:14, was derived from the overlapping and/or extended nucleic acid sequences of Incyte Clone 3440519 (PENCNOT06).

In one embodiment, the invention encompasses a polypeptide comprising the amino acid sequence of SEQ ID NO:7. RASP-7 is 266 amino acids in length and has a region encompassing residues 22 to 222 which resembles the family signature of GTP-binding Ras proteins. Residues 21 to 42, 44 to 60, 61 to 83, and 125 to 138 are similar to the family signatures of transforming protein P21, a GTP-binding Ras protein whose mutations have been implicated in a number of tumors. The ATP/GTP-binding site, motif A (P-loop), encompasses residues G27 to S34. RASP-7 also has four potential casein kinase II phosphorylation sites at S47, S58, S111, and T145; one potential N-myristoylation site at G30; eight potential protein kinase C phosphorylation sites at T37, T42, T80, T123, T211, T242, S245, and S250. RASP-7 has chemical and structural homology with Rit (GI 1656001), a human plasma membrane-associating Ras protein. Specifically, RASP-7 shares about 25% sequence identity with Rit. A fragment of SEQ ID NO:14 from about nucleotide 4 to about nucleotide 65 is useful, for example, as a hybridization probe. Northern analysis shows the expression of this sequence in cardiovascular, nervous, and reproductive cDNA libraries. Approximately 33% of these libraries are associated with cancer, 11% are associated with neurological disorders, and 11% with inflammation and immune response.

The invention also encompasses RASP variants. A preferred RASP variant is one which has at least about 80%, more preferably at least about 90%, and most preferably at least about 95% amino acid sequence identity to the RASP amino acid sequence, and which contains at least one functional or structural characteristic of RASP.

The invention also encompasses polynucleotides which encode RASP. In a particular embodiment, the invention encompasses a polynucleotide sequence comprising the sequence of SEQ ID NO:8, SEQ ID NO:9, SEQ ID NO:10, SEQ ID NO:11, SEQ ID NO:12, SEQ ID NO:13, or SEQ ID NO:14, which encodes an RASP.

The invention also encompasses a variant of a polynucleotide sequence encoding RASP. In particular, such a variant polynucleotide sequence will have at least about 80%, more preferably at least about 90%, and most preferably at least about 95% polynucleotide sequence identity to the polynucleotide sequence encoding RASP. A particular aspect of the invention encompasses a variant of a polynucleotide sequence selected from the group consisting of SEQ ID NO:8, SEQ ID NO:9, SEQ ID NO:10, SEQ ID NO:11, SEQ ID NO:12, SEQ ID NO:13, or SEQ ID NO:14 which has at least about 80%, more preferably at least about 90%, and most preferably at least about 95% polynucleotide sequence identity to a polynucleotide sequence selected from the group consisting of SEQ ID NO:8, SEQ ID NO:9, SEQ ID NO:10, SEQ ID NO:11, SEQ ID NO:12, SEQ ID NO:13, or SEQ ID NO:14. Any one of the polynucleotide variants described above can encode an amino acid sequence which contains at least one functional or structural characteristic of RASP.

It will be appreciated by those skilled in the art that as a result of the degeneracy of the genetic code, a multitude of polynucleotide sequences encoding RASP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring RASP, and all such variations are to be considered as being specifically disclosed.

Although nucleotide sequences which encode RASP and its variants are preferably capable of hybridizing to the nucleotide sequence of the naturally occurring RASP under appropriately selected conditions of stringency, it may be advantageous to produce nucleotide sequences encoding RASP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding RASP and its derivatives without altering the encoded amino acid sequences include the production of RNA transcripts having more desirable properties, such as a greater half-life, than transcripts produced from the naturally occurring sequence.

The invention also encompasses production of DNA sequences which encode RASP and RASP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding RASP or any fragment thereof.

Also encompassed by the invention are polynucleotide sequences that are capable of hybridizing to the claimed polynucleotide sequences, and, in particular, to those shown in SEQ ID NO:1, SEQ ID NO:2, SEQ ID NO:3, or SEQ ID NO:4, SEQ ID NO:5, SEQ ID NO:6, or SEQ ID NO:7, or fragments thereof under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods my employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO BRL, Gaithersburg, Md.). Preferably, the process is automated with machines such as the Hamilton MICROLAB 2200 (Hamilton, Reno, Nev.), Peltier thermal cycler (PTC200; MJ Research, Watertown, Mass.) and the ABI CATALYST and 373 and 377 DNA Sequences (Perkin Elmer).

The nucleic acid sequences encoding RASP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries to walk genomic DNA(Clontech, Palo Alto, Calif.). This procedure avoids the need to screen libraries and is useful in finding intron/exon junctions. For all PCR-based methods, primers may be designed using commercially available software, such as OLIGO™ 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode RASP may be cloned in recombinant DNA molecules that direct expression of RASP, or fragments or functional equivalents thereof, in appropriate host cells. Due to the inherent degeneracy of the genetic code, other DNA sequences which encode substantially the same or a functionally equivalent amino acid sequence may be produced and used to express RASP.

The nucleotide sequences of the present invention can be engineered using methods generally known in the art in order to alter RASP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding RASP may be synthesized, in whole or in part, using chemical methods well known in the art. (See, e.g., Caruthers, M. H. et al. (1980) Nucl. Acids Res. Symp. Ser. 7:215–223, and Horn, T. et al. (1980) Nucl. Acids Res. Symp. Ser. 7:225–232.) Alternatively, RASP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of RASP, or any part thereof, may be altered during direct synthesis and/or combined with sequences from other proteins, or any part thereof, to produce a variant polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active RASP, the nucleotide sequences encoding RASP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding RASP. Such elements may vary in their strength and specificity. Specific initiation signals may also be used to achieve more efficient translation of sequences encoding RASP. Such signals include the ATG initiation codon and adjacent sequences, e.g. the Kozak sequence. In cases where sequences encoding RASP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding RASP and appropriate transcriptional and translational control elements. These methods include in vitro recombinant DNA techniques, synthetic techniques, and in vivo genetic recombination. (See, e.g., Sambrook, J. et al. (1989) *Molecular Cloning A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding RASP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding RASP. For example, routine cloning, subcloning, and propagation of polynucleotide sequences encoding RASP can be achieved us multifunctional *E. coli* vector such as the BLUESCRIPT phagemid (Stratagene) or PSPORT1 plasmid (GIBCO BRL). Ligation of sequences encoding RASP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of RASP are needed, e.g. for the production of antibodies, vectors which direct high level expression of RASP may be used. For example, vectors containing the strong, inducible T5 or T7 bacteriophage promoter may be used.

Yeast expression systems may be used for production of RASP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of RASP. Transcription of sequences encoding RASP may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding RASP may be ligated into an adenovirus transcription/translation complex consisting of the late promoter and tripartite leader sequence. Insertion in a non-essential E1 or E3 region of the viral genome may be used to obtain infective virus which expresses RASP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of RASP in cell lines is preferred. For example, sequences encoding RASP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding RASP is inserted within a marker gene sequence, transformed cells containing sequences encoding RASP can be identified by the absence of marker gene function. Alternatively, a marker gene can be placed in tandem with a sequence encoding RASP under the control of a single promoter. Expression of the marker gene in response to induction or selection usually indicates expression of the tandem gene as well.

In general, host cells that contain the nucleic acid sequence encoding RASP and that express RASP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of RASP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on RASP is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding RASP include oligolabeling, nick translation, end-labeling, or PCR amplification using a labeled nucleotide. Alternatively, the sequences encoding RASP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding RASP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode RASP may be designed to contain signal sequences which direct secretion of RASP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding RASP may be ligated to a heterologous sequence resulting in translation of a fusion protein in any of the aforementioned host systems. For example, a chimeric RASP protein containing a heterologous moiety that can be recognized by a commercially available antibody may facilitate the screening of peptide libraries for inhibitors of RASP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the RASP encoding sequence and the heterologous protein sequence, so that RASP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled RASP may be achieved in vitro using the TNT rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of RASP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of RASP may be synthesized separately and then combined to produce the full length molecule.

Therapeutics

Chemical and structural homology exists among the human Ras proteins of the invention. Northern analysis shows the expression of RASP in cancer and in immune response-associated cDNA libraries. Therefore, RASP appears to play a role in development of cancer and immune disorders.

In one embodiment, an antagonist of RASP may be administered to a subject to treat or prevent a cancer associated with increased expression or activity of RASP. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds RASP may be used directly as an antagonist or indirectly as a targeting or delivery mechanism for bringing a pharmaceutical agent to cells or tissue which express RASP.

In an additional embodiment, a vector expressing the complement of the polynucleotide encoding RASP may be administered to a subject to treat or prevent a cancer including, but not limited to, those described above.

In another embodiment, an antagonist of RASP may be administered to a subject to treat or prevent an immune disorder associated with increased expression or activity of RASP. Such an immune disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, an antibody which specifically binds RASP may be used directly as an antagonist or indirectly as a targeting or delivery mechanism for bringing a pharmaceutical agent to cells or tissue which express RASP.

In an additional embodiment, a vector expressing the complement of the polynucleotide encoding RASP may be administered to a subject to treat or prevent an immune disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of RASP may be produced using methods which are generally known in the art. In particular, purified RASP may be used to produce antibodies or to screen libraries of pharmaceutical agents to identify those which specifically bind RASP. Antibodies to RASP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with RASP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to RASP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of RASP amino acids may be fused with those of another protein, such as KLH, and antibodies to the chimeric molecule may be produced.

Monoclonal antibodies to RASP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M.S. et al. (1984) Nature 312:604–608; and Takeda, S. et al. (1985) Nature 314:452–454.) Alternatively, techniques described for the production of single chain antibodies may be adapted, using methods known in the art, to produce RASP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for RASP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between RASP and its specific antibody. A two-site, monoclonal-based immunoassay utilizing monoclonal antibodies reactive to two non-interfering RASP epitopes is preferred, but a competitive binding assay may also be employed. (Maddox, supra.)

In another embodiment of the invention, the polynucleotides encoding RASP, or any fragment or complement thereof, may be used for therapeutic purposes. In one aspect, the complement of the polynucleotide encoding RASP may be used in situations in which it would be desirable to block the transcription of the mRNA. In particular, cells may be transformed with sequences complementary to polynucleotides encoding RASP. Thus, complementary molecules or fragments may be used to modulate RASP activity, or to achieve regulation of gene function. Such technology is now well known in the art, and sense or antisense oligonucleotides or larger fragments can be designed from various locations along the coding or control regions of sequences encoding RASP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding RASP. (See, e.g., Sambrook, supra; and Ausubel, supra.)

Genes encoding RASP can be turned off by transforming a cell or tissue with expression vectors which express high levels of a polynucleotide, or fragment thereof, encoding RASP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding RASP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding RASP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding RASP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of RASP, antibodies to RASP, and mimetics, agonists, antagonists, or inhibitors of RASP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e.,.dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of RASP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example RASP or fragments thereof, antibodies of RASP, and agonists, antagonists or inhibitors of RASP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $LD_{50}ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind RASP may be used for the diagnosis of disorders characterized by expression of RASP, or in assays to monitor patients being treated with RASP or agonists, antagonists, or inhibitors of RASP. Antibodies useful for diagnostic purposes may be prepared in the same manner as described above for therapeutics. Diagnostic assays for RASP include methods which utilize the antibody and a label to detect RASP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring RASP, including ELISAs, RIAs, and FACS, are known in the art and provide a basis for diagnosing altered or abnormal levels of RASP expression. Normal or standard values for RASP expression are established by combining body fluids or cell extracts taken from normal mammalian subjects, preferably human, with antibody to RASP under conditions suitable for complex formation. The amount of standard complex formation may be quantitated by various methods, preferably by photometric means. Quantities of RASP expressed in subject, control, and disease samples from biopsied tissues are compared with the standard values. Deviation between standard and subject values establishes the parameters for diagnosing disease.

In another embodiment of the invention, the polynucleotides encoding RASP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of RASP may be correlated with disease. The diagnostic assay may be used to determine absence, presence, and excess expression of RASP, and to monitor regulation of RASP levels during therapeutic intervention.

In one aspect, hybridization with PCR probes which are capable of detecting polynucleotide sequences, including genomic sequences, encoding RASP or closely related molecules may be used to identify nucleic acid sequences which encode RASP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding RASP, allelic variants, or related sequences.

Probes may also be used for the detection of related sequences, and should preferably have at least 50% sequence identity to any of the RASP encoding sequences. The hybridization probes of the subject invention may be DNA or RNA and may be derived from the sequence of SEQ ID NO:8, SEQ ID NO:9, SEQ ID NO:10, SEQ ID NO:11, SEQ ID NO:12, SEQ ID NO:13, or SEQ ID NO:14, or from genomic sequences including promoters, enhancers, and introns of the RASP gene.

Means for producing specific hybridization probes for DNAs encoding RASP include the cloning of polynucleotide sequences encoding RASP or RASP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}p$ or $^{35}S$, or by enzymatic labels, such as alkaline phosphatase coupled to the probe via avidin/biotin coupling systems, and the like.

Polynucleotide sequences encoding RASP may be used for the diagnosis of a disorder associated with expression of RASP. Examples of such a disorder include, but are not limited to, cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immune disorders such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding RASP may be used in Southern or northern analysis, dot blot, or other membrane-based technologies; in PCR technologies; in dipstick, pin, and ELISA assays; and in microarrays utilizing fluids or tissues from patients to detect altered RASP expression. Such qualitative or quantitative methods are well known in the art.

In a particular aspect, the nucleotide sequences encoding RASP may be useful in assays that detect the presence of associated disorders, particularly those mentioned above. The nucleotide sequences encoding RASP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding RASP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of RASP, a normal or standard profile for expression is established. This may be accomplished by combining body fluids or cell extracts taken from normal subjects, either animal or human, with a sequence, or a fragment thereof, encoding RASP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding RASP may involve the use of PCR. These oligomers may be chemically synthesized, generated enzymatically, or produced in vitro. Oligomers will preferably contain a fragment of a polynucleotide encoding RASP, or a fragment of a polynucleotide complementary to the polynucleotide encoding RASP, and will be employed under optimized conditions for identification of a specific gene or condition. Oligomers may also be employed under less stringent conditions for detection or quantitation of closely related DNA or RNA sequences.

Methods which may also be used to quantitate the expression of RASP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application W095/251116; Shalon, D. et al. (1995) PCT application WO95/35505; Heller, R. A. et al.

(1997) Proc. Natl. Acad. Sci. 94:2150–2155; and Heller, M. J. et al. (1997) U.S. Pat. No. 5,605,662.)

In another embodiment of the invention, nucleic acid sequences encoding RASP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding RASP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, RASP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between RASP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with RASP, or fragments thereof, and washed. Bound RASP is then detected by methods well known in the art. Purified RASP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding RASP specifically compete with a test compound for binding RASP. In this manner, antibodies can be used to detect the presence of any peptide which shares one or more antigenic determinants with RASP.

In additional embodiments, the nucleotide sequences which encode RASP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

RNA was purchased from Clontech (Palo Alto, Calif.) or isolated at Incyte from tissues described in Table 4. The tissue was homogenized, lysed, and extracted in phenol guanidinium isothiocyanate, or a suitable mixture of denaturants such as TRIZOL reagent (Life Technologies, Gaithersburg, Md.), a monophasic solution of phenol and guanidine isothiocyanate. To isolate RNA, lysate was centrifuged over a CsCl cushion, mixed with chloroform (1:5 v/v), and recovered in the aqueous phase. Alternatively, lysate was electrophoresed through an agarose gel, and RNA was collected using Whatman P81 paper (Whatman, Lexington Mass.) and eluted. The recovered RNA was precipitated with isopropanol,the eluted RNA, with sodium acetate and ethanol, and the precipitant was resuspended in RNase-free water. For some libraries, RNA was treated with DNase; and for others, phenol extraction and precipitation were repeated. For most libraries, poly(A+) RNA was isolated oligo d(T)-coupled paramagnetic particles (Promega, Madison, Wis.), OLIGOTEX Resin, or the OLIGOTEX kit (QIAGEN Inc, Chatsworth, Calif.). Alternatively RNA was isolated directly from tissue lysates using the Ambion POLY QUICK kit (Ambion, Austin, Tex.).

RNA was used for cDNA synthesis and construction of the cDNA libraries according to procedures recommended in the UNIZAP (Stratagene, La Jolla, Calif.) or SUPERSCRIPT plasmid system (Life Technologies, Inc), both of which are based on methods well known in the art (Ausubel, supra, units 5.1–6.6). Alternatively, cDNA libraries were constructed by Stratagene using RNA provided by Incyte. Reverse transcription was initiated using oligo d(T) or random primers. Synthetic oligonucleotide adapters were ligated to double stranded cDNA, and cDNA was digested with an appropriate restriction enzyme(s). For most libraries cDNA was size-selected (300–1000 bp) using SEPHACRYL S1000 or SEPHAROSE CL2B or CL4B column chromatography (Amersham Pharmacia Biotech) or preparative agarose gel electrophoresis. cDNAs were ligated into compatible restriction enzyme site of the polylinker of a suitable plasmid, e.g., BLUESCRIPT phagemid (Stratagene), PSPORT1 (Life Technologies), pINCY1 (Incyte Pharmaceuticals Inc Palo Alto, Calif.). pINCY1 was amplified in JM109 cells and purified using the QIAQUICK column (QIAGEN Inc). Recombinant plasmids were transformed into competent *E. coli* cells, e.g., XL1-BLUE, XL1-BLUE MRF, or SOLR (Stratagene) or DH5α; DH10B, or ELECTROMAX DH10B (Life Technologies).

TABLE 4

| Clone Number | Library Name | Library Source |
|---|---|---|
| 627565 | KIDNNOT05 | Constructed using polyA RNA isolated from the kidney tissue of a 2-day-old Hispanic female, who died from cerebral anoxia. |
| 775601 | COLNNOT05 | Constructed using polyA RNA isolated from the normal sigmoid colon tissue of a 40-year-old Caucasian male during a partial colectomy. |
| 1528559 | UCMCL5T01 | Constructed using polyA RNA isolated from mononuclear cells obtained from the umbilical cord blood of 12 individuals. The cells were cultured for 12 days with IL-5 before RNA was obtained from the pooled lysates. |
| 1651593 | PROSTUT08 | Constructed using polyA RNA isolated from prostate tumor tissue removed from a 60-year-old Caucasian male during radical prostatectomy and regional lymph node excision. |
| 1673056 | BLADNOT05 | Constructed using polyA RNA isolated from nontumorous bladder tissue removed from a 60-year-old Caucasian male during a radical cystectomy, prostatectomy, and vasectomy. |
| 2703745 | OVARTUT10 | Constructed using polyA RNA isolated from ovarian tumor tissue removed from the left ovary of a 58-year-old Caucasian female during a total abdominal hysterectomy, removal of a solitary ovary, and repair of inguinal hernia. |
| 3440519 | PENCNOT06 | Constructed using polyA RNA isolated from corpora cavernosa tissue removed from a 3-year-old Black male. Pathology indicated surgical margins were free of neoplasm. |

II. Isolation and Sequencing of cDNA Clones

Plasmids were recovered from host cells by in vivo excision (UNIZAP vector system, Stratagene) or by cell lysis. Plasmids were purified using the MAGIC MINI-PREPS DNA purification system (Promega, Madison, Wis.); MINIPREP kit (Advanced Genetic Technologies Corporation, Gaithersburg, Md.); QIAWELL b 8Plasmid, QIAWELL PLUS DNA, or QIAWELL ULTRA DNA purification systems; or R.E.A.L.PREP 96 plasmid kit (QIAGEN Inc) using the recommended protocol. Following precipitation, plasmids were resuspended in 0.1 ml of distilled water and stored, with or without lyophilization, at 4° C.

Alternatively, plasmid DNA was amplified from host cell lysates using direct link PCR (Rao, V. B. (1994) Anal. Biochem. 216:1–14) in a high-throughput format. Host cell lysis and thermal cycling steps were carried out in a single reaction mixture. Samples were processed and stored in 384-well plates ((Genetix Ltd, Christchurch UK) and concentration of amplified plasmid DNA was quantified fluorometrically using PICO GREEN Dye (Molecular Probes, Eugene Oreg.) and a FLOUROSCAN II fluorescence scanner (Labsystems Oy, Helsinki, Finland).

Samples were prepared for sequencing using a CATALYST 800 or a Hamilton MICROLAB 2200 or Robbins HYDRALAB 2200 (Hamilton, Reno Nev.) in combination with Peltier thermal cyclers (PTC200 from MJ Research, Watertown Mass.). cDNAs were sequenced by the method of Sanger, F. and A. R. Coulson (1975; J. Mol. Biol. 94:441–448) on ABI 373 and 377 DNA sequencing systems (Perkin Elmer). Most cDNAs were sequenced according to standard ABI protocols, using ABI kits and reagents (Cat. #79345, 79339, 79340, 79357, 79355). The solution volumes were adjusted for 0.25×–1.0× reagent concentration. Alternatively, cDNAs were sequenced using solutions and dyes from Amersham Pharmacia Biotech.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff S. And Henikoff G. J., Nucleic Acids Research (1991) 19:6565–6572.) Blocks, which are 3–60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probalistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding RASP occurs. Abundance and percent abundance are also reported. Abundance directly reflects the number of times a particular transcript is represented in a cDNA library, and percent abundance is abundance divided by the total number of sequences examined in the cDNA library.

V. Extension of RASP Encoding Polynucleotides

The sequence of one of the polynucleotides of the present invention was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 primer analysis software (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |

-continued

| Step 9  | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using the QIAQUICK DNA purification kit (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 1° C. Competent *E. coli* cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing 2×Carb. The following day, several colonies were randomly picked from each plate and cultured in 150 μl of liquid LB/2×Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:8, SEQ ID NO:9, SEQ ID NO:10, SEQ ID NO:11, SEQ ID NO:12, SEQ ID NO:13, or SEQ ID NO:14, are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:8, SEQ ID NO:9, SEQ ID NO:10, SEQ ID NO:11, SEQ ID NO:12, SEQ ID NO:13, or SEQ ID NO:14 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 primer analysis software (National Biosciences) and labeled by combining 50 pmol of each oligomer, 250 μCi of [γ-$^{32}$P]adenosine triphosphate (Amersham, Chicago, Ill.), and T4 polynucleotide kinase (DuPont NEN®, Boston, Mass.). The labeled oligonucleotides are substantially purified using a SEPHADEX G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN, Boston, Mass.).

The DNA from each digest is fractionated on a 0.7 percent agarose gel and transferred to nylon membranes (NYTRAN PLUS membrane, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR auto radiography film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the RASP-encoding sequences, or any parts thereof, are used to detect, decrease, or inhibit expression of naturally occurring RASP. Although use of oligonucleotides comprising from about 15 to 30 base pairs is described, essentially the same procedure is used with smaller or with larger sequence fragments. Appropriate oligonucleotides are designed using OLIGO™ 4.06 primer analysis software and the coding sequence of RASP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the RASP-encoding transcript.

IX. Expression of RASP

Expression and purification of RASP is achieved using bacterial or virus-based expression systems. For expression of RASP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express RASP upon induction with isopropyl beta-D-thiogalactopyranoside (IPTG). Expression of RASP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding RASP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, RASP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 2-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from RASP at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified RASP obtained by these methods can be used directly in the following activity assay.

X. Demonstration of RASP Activity

RASP can be expressed in a mammalian cell line such as 293T by transfecting with an eukaryotic expression vector encoding RASP. Eukaryotic expression vectors are commercially available, and the techniques to introduce them into cells are well known to those skilled in the art. A small amount of a second plasmid, which expresses any one of a number of reporter genes such as β-galactosidase, is co-transformed into the cells in order to allow rapid identification of those cells which have taken up and expressed the foreign DNA. The cells are cultured in a defined synthetic medium with varying concentrations of GTP for at least 48 hours after transformation to allow expression and accumulation of RASP and β-galactosidase.

Transformed cells expressing β-galactosidase are stained blue when a suitable colorimetric substrate is added to the culture media under conditions that are well known in the art. Increasing concentrations of GTP induces increasing numbers of reporter gene positive cells (Ren, M. et al. (1996) Proc. Natl. Acad. Sci. 93: 5151–5155). GTP-treated cells which were not transformed with the RASP expression vector are used as controls, so are RASP transfected cells cultured without supplemental GTP.

XI. Functional Assays

RASP function is assessed by expressing the sequences encoding RASP at physiologically elevated levels in mammalian cell culture systems. cDNA is subcloned into a mammalian expression vector containing a strong promoter that drives high levels of cDNA expression. Vectors of choice include PCMV SPORTS (Life Technologies, Gaithersburg, Md.) and PCR 3.1 (Invitrogen, Carlsbad, Calif., both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of RASP on gene expression can be assessed using highly purified populations of cells transfected with sequences encoding RASP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding RASP and other genes of interest can be analyzed by Northern analysis or microarray techniques.

XII. Production of RASP Specific Antibodies

RASP substantially purified using polyacrylamide gel electrophoresis (PAGE) (see, e.g., Harrington, M. G. (1990) Methods Enzymol. 182:488–495), or other purification techniques, is used to immunize rabbits and to produce antibodies using standard protocols.

Alternatively, the RASP amino acid sequence is analyzed using LASERGENE software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring RASP Using Specific Antibodies

Naturally occurring or recombinant RASP is substantially purified by immunoaffinity chromatography using antibodies specific for RASP. An immunoaffinity column is constructed by covalently coupling anti-RASP antibody to an activated chromatographic resin, such as CNBr-activated SEPHAROSE (Pharmacia & Upjohn). After the coupling, the resin is blocked and washed according to the manufacturer's instructions.

Media containing RASP are passed over the immunoaffinity column, and the column is washed under conditions that allow the preferential absorbance of RASP (e.g., high ionic strength buffers in the presence of detergent). The column is eluted under conditions that disrupt antibody/RASP binding (e.g., a buffer of pH 2 to pH 3, or a high concentration of a chaotrope, such as urea or thiocyanate ion), and RASP is collected.

XIV. Identification of Molecules Which Interact with RASP

RASP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled RASP, washed, and any wells with labeled RASP complex are assayed. Data obtained using different concentrations of RASP are used to calculate values for the number, affinity, and association of RASP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding the polypeptide of SEQ ID NO:1 or SEQ ID NO:4.

2. An isolated and purified polynucleotide having a sequence which is fully complementary to the polynucleotide sequence of claim 1.

3. An isolated and purified polynucleotide comprising a polynucleotide sequence selected from the group consisting of SEQ ID NO:8 and SEQ ID NO:11.

4. An isolated and purified polynucleotide having a sequence which is fully complementary to the polynucleotide of claim 3.

5. An expression vector comprising the polynucleotide of claim 1.

6. A host cell comprising the expression vector of claim 5.

7. A method for producing a polypeptide comprising the amino acid sequence selected from the group consisting of SEQ ID NO:1 and SEQ ID NO:4, the method comprising the steps of:

a) culturing the host cell of claim 6 under conditions suitable for the expression of the polypeptide; and b) recovering the polypeptide from the host cell culture.

8. A method for detecting a polynucleotide encoding the polypeptide comprising the amino acid sequence selected from the group consisting of SEQ ID NO:1 and SEQ ID NO:4 in a biological sample, the method comprising the steps of:
(a) hybridizing the polynucleotide of claim 2 to at least one of the nucleic acids in the biological sample, thereby forming a hybridization complex;
(b) washing said hybridization complex at room temperature under increasingly stringent conditions up to 0.1× saline sodium citrate and 0.5% sodium dodecyl sulfate; and
(c) detecting the hybridization complex, wherein the presence of the hybridization complex correlates with the presence of the polynucleotide encoding the polypeptide in the biological sample.

9. The method of claim 8 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 14

(2) INFORMATION FOR SEQ ID NO:      1:

(i) SEQUENCE CHARACTERISTICS:
        (A) LENGTH: 259 amino acids
        (B) TYPE: amino acid
        (C) STRANDEDNESS: single
        (D) TOPOLOGY: linear (vii) IMMEDIATE SOURCE:
        (A) LIBRARY: KIDNNOT05
        (B) CLONE: 627565

(xi) SEQUENCE DESCRIPTION: SEQ ID NO: 1 :

Met Asn Ile Leu Ala Pro Val Arg Arg Asp A rg Val Leu Ala Glu
               5               10               15

Leu Pro Gln Cys Leu Arg Lys Glu Ala Ala L eu His Gly His Lys
              20              25              30

Asp Phe His Pro Arg Val Thr Cys Ala Cys G ln Glu His Arg Thr
              35              40              45

Gly Thr Val Gly Phe Lys Ile Ser Lys Val I le Val Val Gly Asp
              50              55              60

Leu Ser Val Gly Lys Thr Cys Leu Ile Asn A rg Phe Cys Lys Asp
              65              70              75

Thr Phe Asp Lys Asn Tyr Lys Ala Thr Ile G ly Val Asp Phe Glu
              80              85              90

-continued

```
Met Glu Arg Phe Glu Val Leu Gly Ile Pro Phe Ser Leu Gln Leu
                 95                 100                 105

Trp Asp Thr Ala Gly Gln Glu Arg Phe Lys Cys Ile Ala Ser Thr
            110                 115                 120

Tyr Tyr Arg Gly Ala Gln Ala Ile Ile Val Phe Asn Leu Asn
            125                 130                 135

Asp Val Ala Ser Leu Glu His Thr Lys Gln Trp Leu Ala Asp Ala
            140                 145                 150

Leu Lys Glu Asn Asp Pro Ser Ser Val Leu Leu Phe Leu Val Gly
            155                 160                 165

Ser Lys Lys Asp Leu Ser Thr Pro Ala Gln Tyr Ala Leu Met Glu
            170                 175                 180

Lys Asp Ala Leu Gln Val Ala Gln Glu Met Lys Ala Glu Tyr Trp
            185                 190                 195

Ala Val Ser Ser Leu Thr Gly Glu Asn Val Arg Glu Phe Phe
            200                 205                 210

Arg Val Ala Ala Leu Thr Phe Glu Ala Asn Val Leu Ala Glu Leu
            215                 220                 225

Glu Lys Ser Gly Ala Arg Arg Ile Gly Asp Val Val Arg Ile Asn
            230                 235                 240

Ser Asp Asp Ser Asn Leu Tyr Leu Thr Ala Ser Lys Lys Pro
            245                 250                 255

Thr Cys Cys Pro (2) INFORMATION FOR SEQ ID NO:    2:

(i) SEQUENCE CHARACTERISTICS:
        (A) LENGTH: 196 amino acids
        (B) TYPE: amino acid
        (C) STRANDEDNESS: single
        (D) TOPOLOGY: linear (vii) IMMEDIATE SOURCE:
        (A) LIBRARY: COLNNOT05
        (B) CLONE: 775601

(xi) SEQUENCE DESCRIPTION: SEQ ID NO: 2 :

Met Gly Ile Leu Phe Thr Arg Ile Trp Arg Leu Phe Asn His Gln
                 5                  10                  15

Gly Pro Arg Gly Ser Ser Gln Thr Asn Ala Ala Ala Met Ser Ala
            20                  25                  30

Ser Leu Glu His Lys Val Ile Ile Val Gly Leu Asp Asn Ala Gly
            35                  40                  45

Lys Thr Thr Ile Leu Tyr Gln Phe Ser Met Asn Glu Val Val His
            50                  55                  60

Thr Ser Pro Thr Ile Gly Gly Asn Val Glu Glu Ile Ala Ile Asn
            65                  70                  75

Asn Thr Arg Phe Leu Met Trp Asp Ile Gly Gly Gln Glu Ser Leu
            80                  85                  90

Arg Ser Ser Trp Asn Thr Tyr Tyr Thr Asn Thr Glu Phe Val Ile
            95                  100                 105

Val Val Asp Ser Thr Asp Arg Glu Arg Ile Ser Val Thr Arg
            110                 115                 120

Glu Glu Leu Tyr Lys Met Leu Ala His Glu Asp Pro Arg Lys Ala
            125                 130                 135

Gly Leu Leu Ile Phe Ala Asn Lys Gln Asp Val Lys Glu Cys Met
            140                 145                 150
```

```
Thr Val Ala Glu Ile Ser Gln Phe Leu Lys L eu Thr Ser Ile Lys
                155                 160                 165

Asp His Gln Trp His Ile Gln Ala Cys Cys A la Leu Thr Gly Glu
                170                 175                 180

Gly Leu Cys Gln Gly Leu Glu Trp Met Met S er Arg Leu Lys Ile
                185                 190                 195

Arg (2) INFORMATION FOR SEQ ID NO:       3:

(i) SEQUENCE CHARACTERISTICS:
        (A) LENGTH: 191 amino acids
        (B) TYPE: amino acid
        (C) STRANDEDNESS: single
        (D) TOPOLOGY: linear (vii) IMMEDIATE SOURCE:
         (A) LIBRARY: UCMCL5T01
         (B) CLONE: 1528559

(xi) SEQUENCE DESCRIPTION: SEQ ID NO: 3 :

Met Leu Leu Gly Asp Thr Gly Val Gly Lys T hr Cys Phe Leu Ile
                 5                  10                  15

Gln Phe Lys Asp Gly Ala Phe Leu Ser Gly T hr Phe Ile Ala Thr
                20                  25                  30

Val Gly Ile Asp Phe Arg Asn Lys Val Val T hr Val Asp Gly Val
                35                  40                  45

Arg Val Lys Leu Gln Ile Trp Asp Thr Ala G ly Gln Glu Arg Phe
                50                  55                  60

Arg Ser Val Thr His Ala Tyr Tyr Arg Asp A la Gln Ala Leu Leu
                65                  70                  75

Leu Leu Tyr Asp Ile Thr Asn Lys Ser Ser P he Asp Asn Ile Arg
                80                  85                  90

Ala Trp Leu Thr Glu Ile His Glu Tyr Ala G ln Arg Asp Val Val
                95                  100                 105

Ile Met Leu Leu Gly Asn Lys Ala Asp Met S er Ser Glu Arg Val
                110                 115                 120

Ile Arg Ser Glu Asp Gly Glu Thr Leu Ala A rg Glu Tyr Gly Val
                125                 130                 135

Pro Phe Leu Glu Thr Ser Ala Lys Thr Gly M et Asn Val Glu Leu
                140                 145                 150

Ala Phe Leu Ala Ile Ala Lys Glu Leu Lys T yr Arg Ala Gly His
                155                 160                 165

Gln Ala Asp Glu Pro Ser Phe Gln Ile Arg A sp Tyr Val Glu Ser
                170                 175                 180

Gln Lys Lys Arg Ser Ser Cys Cys Ser Phe M et
                185                 190

(2) INFORMATION FOR SEQ ID NO:       4:

(i) SEQUENCE CHARACTERISTICS:
        (A) LENGTH: 260 amino acids
        (B) TYPE: amino acid
        (C) STRANDEDNESS: single
        (D) TOPOLOGY: linear (vii) IMMEDIATE SOURCE:
         (A) LIBRARY: PROSTUT08
         (B) CLONE: 1651593
```

(xi) SEQUENCE DESCRIPTION: SEQ ID NO: 4 :

```
Met Asn Ile Leu Ala Pro Val Arg Arg Asp Arg Val Leu Ala Glu
                  5                  10                  15

Leu Pro Gln Cys Leu Arg Lys Glu Ala Ala Leu His Gly His Lys
                 20                  25                  30

Asp Phe His Pro Arg Val Thr Cys Ala Cys Gln Glu His Arg Thr
                 35                  40                  45

Gly Thr Val Gly Arg Phe Lys Ile Ser Lys Val Ile Val Val Gly
                 50                  55                  60

Asp Leu Ser Val Gly Lys Thr Cys Leu Ile Asn Arg Phe Cys Lys
                 65                  70                  75

Asp Thr Phe Asp Lys Asn Tyr Lys Ala Thr Ile Gly Val Asp Phe
                 80                  85                  90

Glu Met Glu Arg Phe Glu Val Leu Gly Ile Pro Phe Ser Leu Gln
                 95                 100                 105

Leu Trp Asp Thr Ala Gly Gln Glu Arg Phe Lys Cys Ile Ala Ser
                110                 115                 120

Thr Tyr Tyr Arg Gly Ala Gln Ala Ile Ile Ile Val Phe Asn Leu
                125                 130                 135

Asn Asp Val Ala Ser Leu Glu His Thr Lys Gln Trp Leu Ala Asp
                140                 145                 150

Ala Leu Lys Glu Asn Asp Pro Ser Ser Val Leu Leu Phe Leu Val
                155                 160                 165

Gly Ser Lys Lys Asp Leu Ser Thr Pro Ala Gln Tyr Ala Leu Met
                170                 175                 180

Glu Lys Asp Ala Leu Gln Val Ala Gln Glu Met Lys Ala Glu Tyr
                185                 190                 195

Trp Ala Val Ser Ser Leu Thr Gly Glu Asn Val Arg Glu Phe Phe
                200                 205                 210

Phe Arg Val Ala Ala Leu Thr Phe Glu Ala Asn Val Leu Ala Glu
                215                 220                 225

Leu Glu Lys Ser Gly Ala Arg Arg Ile Gly Asp Val Val Arg Ile
                230                 235                 240

Asn Ser Asp Asp Ser Asn Leu Tyr Leu Thr Ala Ser Lys Lys Lys
                245                 250                 255

Pro Thr Cys Cys Pro
                260
```

(2) INFORMATION FOR SEQ ID NO: 5:

(i) SEQUENCE CHARACTERISTICS:
        (A) LENGTH: 190 amino acids
        (B) TYPE: amino acid
        (C) STRANDEDNESS: single
        (D) TOPOLOGY: linear (vii) IMMEDIATE SOURCE:
        (A) LIBRARY: BLADNOT05
        (B) CLONE: 1673056

(xi) SEQUENCE DESCRIPTION: SEQ ID NO: 5 :

```
Met Leu Pro Ile Phe Ile Ser Asn Trp Trp Leu Asp Met Leu Gly
                  5                  10                  15

Leu Val Trp Glu Pro Ser Asp Lys Leu Lys Gly Trp Ile Arg Lys
                 20                  25                  30

Arg Leu Thr Thr Pro Leu Val Ala Gly Gln Glu Asp Tyr Asp Arg
                 35                  40                  45
```

```
Leu Arg Thr Leu Ser Tyr Pro Gln Thr Val G ly Glu Thr Tyr Gly
                50                  55                      60

Lys Asp Ile Thr Ser Arg Gly Lys Asp Met P ro Ile Ala Asp Val
                65                  70                      75

Phe Leu Ile Cys Phe Ser Leu Val Ser Pro A la Ser Phe Glu Asn
                80                  85                      90

Val Arg Ala Lys Trp Tyr Pro Glu Val Arg H is His Cys Pro Asn
                95                  100                     105

Thr Pro Ile Ile Leu Val Gly Thr Lys Leu A sp Leu Arg Asp Asp
                110                 115                     120

Lys Asp Thr Ile Glu Lys Leu Lys Glu Lys L ys Leu Thr Pro Ile
                125                 130                     135

Thr Tyr Pro Gln Gly Leu Ala Met Ala Lys G lu Ile Gly Ala Val
                140                 145                     150

Lys Tyr Leu Glu Cys Ser Ala Leu Thr Gln A rg Gly Leu Lys Thr
                155                 160                     165

Val Phe Asp Glu Ala Ile Arg Ala Val Ile C ys Pro Pro Pro Val
                170                 175                     180

Lys Lys Arg Lys Arg Lys Cys Leu Met Leu
                185                 190

(2) INFORMATION FOR SEQ ID NO:    6:

(i) SEQUENCE CHARACTERISTICS:
          (A) LENGTH: 211 amino acids
          (B) TYPE: amino acid
          (C) STRANDEDNESS: single
          (D) TOPOLOGY: linear (vii) IMMEDIATE SOURCE:
          (A) LIBRARY: OVARTUT10
          (B) CLONE: 2703745

(xi) SEQUENCE DESCRIPTION: SEQ ID NO: 6 :

Met Thr Thr Leu Asn Leu Leu Ala His Arg A rg Leu Thr Arg Leu
                5                   10                      15

Tyr Leu Leu Gly Thr Leu Gln Trp Gly Ser L eu Val Ser Ser Trp
                20                  25                      30

Arg Leu Cys Lys Asn Glu Phe Arg Glu Asn I le Ser Ala Thr Leu
                35                  40                      45

Gly Val Asp Phe Gln Met Lys Thr Leu Ile V al Asp Gly Glu Arg
                50                  55                      60

Thr Val Leu Gln Leu Trp Asp Thr Ala Gly G ln Glu Arg Phe Arg
                65                  70                      75

Ser Ile Ala Lys Ser Tyr Phe Arg Lys Ala A sp Gly Val Leu Leu
                80                  85                      90

Leu Tyr Asp Val Thr Cys Glu Lys Ser Phe L eu Asn Ile Arg Glu
                95                  100                     105

Trp Val Asp Met Ile Glu Asp Ala Ala His G lu Thr Val Pro Ile
                110                 115                     120

Met Leu Val Gly Asn Lys Ala Asp Ile Arg A sp Thr Ala Ala Thr
                125                 130                     135

Glu Gly Gln Lys Cys Val Pro Gly His Phe G ly Glu Lys Leu Ala
                140                 145                     150

Met Thr Tyr Gly Ala Leu Phe Cys Glu Thr S er Ala Lys Asp Gly
                155                 160                     165
```

-continued

```
Ser Asn Ile Val Glu Ala Val Leu His Leu Ala Arg Glu Val Lys
                170                 175                 180

Lys Arg Thr Asp Lys Asp Asp Ser Arg Ser Ile Thr Asn Leu Thr
                185                 190                 195

Gly Thr Asn Ser Lys Lys Ser Pro Gln Met Lys Asn Cys Cys Asn
                200                 205                 210

Gly (2) INFORMATION FOR SEQ ID NO:      7:

(i) SEQUENCE CHARACTERISTICS:
        (A) LENGTH: 266 amino acids
        (B) TYPE: amino acid
        (C) STRANDEDNESS: single
        (D) TOPOLOGY: linear (vii) IMMEDIATE SOURCE:
        (A) LIBRARY: PENCNOT06
        (B) CLONE: 3440519

(xi) SEQUENCE DESCRIPTION: SEQ ID NO: 7 :

Met Ser Ser Val Phe Gly Lys Pro Arg Ala Gly Ser Gly Pro Gln
                  5                  10                  15

Ser Ala Pro Leu Glu Val Asn Leu Ala Ile Leu Gly Arg Arg Gly
                 20                  25                  30

Ala Gly Lys Ser Ala Leu Thr Val Lys Phe Leu Thr Lys Arg Phe
                 35                  40                  45

Ile Ser Glu Tyr Asp Pro Asn Leu Glu Asp Thr Tyr Ser Ser Glu
                 50                  55                  60

Glu Thr Val Asp His Gln Pro Val His Leu Arg Val Met Asp Thr
                 65                  70                  75

Ala Asp Leu Asp Thr Pro Arg Asn Cys Glu Arg Tyr Leu Asn Trp
                 80                  85                  90

Ala His Ala Phe Leu Val Val Tyr Ser Val Asp Ser Arg Gln Ser
                 95                 100                 105

Phe Asp Ser Ser Ser Ser Tyr Leu Glu Leu Leu Ala Leu His Ala
                110                 115                 120

Lys Glu Thr Gln Arg Ser Ile Pro Ala Leu Leu Leu Gly Asn Lys
                125                 130                 135

Leu Asp Met Ala Gln Tyr Arg Gln Val Thr Lys Ala Glu Gly Val
                140                 145                 150

Ala Leu Ala Gly Arg Phe Gly Cys Leu Phe Phe Glu Val Ser Ala
                155                 160                 165

Cys Leu Asp Phe Glu His Val Gln His Val Phe His Glu Ala Val
                170                 175                 180

Arg Glu Ala Arg Arg Glu Leu Glu Lys Ser Pro Leu Thr Arg Pro
                185                 190                 195

Leu Phe Ile Ser Glu Glu Arg Ala Leu Pro His Gln Ala Pro Leu
                200                 205                 210

Thr Ala Arg His Gly Leu Ala Ser Cys Thr Phe Asn Thr Leu Ser
                215                 220                 225

Thr Ile Asn Leu Lys Glu Met Pro Thr Val Ala Gln Ala Lys Leu
                230                 235                 240

Val Thr Val Lys Ser Ser Arg Ala Gln Ser Lys Arg Lys Ala Pro
                245                 250                 255

Thr Leu Thr Leu Leu Lys Gly Phe Lys Ile Phe
                260                 265
```

(2) INFORMATION FOR SEQ ID NO: 8:

(i) SEQUENCE CHARACTERISTICS:
        (A) LENGTH: 1172 base pairs
        (B) TYPE: nucleic acid
        (C) STRANDEDNESS: single
        (D) TOPOLOGY: linear (vii) IMMEDIATE SOURCE:
        (A) LIBRARY: KIDNNOT05
        (B) CLONE: 627565

(xi) SEQUENCE DESCRIPTION: SEQ ID NO: 8 :

```
GGCGCCCTGC AAGGCCGCAG GCAGGATGAA CATTCTGGCA CCCGTGCGGA G GGATCGCGT      60

CCTGGCGGAG CTGCCCCAGT GCCTGAGGAA GGAGGCCGCT TTGCACGGGC A CAAAGACTT     120

CCACCCCCGC GTCACCTGCG CCTGCCAGGA GCACCGGACA GGCACCGTGG G ATTTAAGAT     180

CTCCAAGGTC ATTGTGGTGG GGGACCTGTC GGTGGGGAAG ACTTGCCTCA T TAATAGGTT     240

CTGCAAAGAC ACCTTTGATA AGAATTACAA GGCCACCATT GGAGTGGACT T CGAGATGGA     300

ACGATTTGAG GTGCTGGGCA TTCCCTTCAG TTTGCAGCTT TGGGATACCG C TGGGCAGGA     360

GAGGTTCAAA TGCATTGCAT CAACCTACTA TAGAGGAGCT CAAGCCATCA T CATTGTCTT     420

CAACCTGAAT GATGTGGCAT CTCTGGAACA TACCAAGCAG TGGCTGGCCG A TGCCCTGAA     480

GGAGAATGAC CCTTCCAGTG TGCTTCTCTT CCTTGTAGGT TCCAAGAAGG A TCTGAGTAC     540

CCCTGCTCAG TATGCGCTGA TGGAGAAAGA CGCCCTCCAG GTGGCCCAGG A GATGAAGGC     600

TGAGTACTGG GCAGTCTCAT CTCTCACTGG TGAGAATGTC CGAGAATTCT T CTTCCGTGT     660

GGCAGCACTG ACCTTTGAGG CCAATGTGCT GGCTGAGCTG GAGAAATCGG G GGCTCGACG     720

CATTGGGGAT GTTGTCCGCA TCAACAGTGA TGACAGCAAC CTCTACCTAA C TGCCAGCAA     780

GAAGAAGCCC ACATGTTGCC CATGAGGGCT GAGGAGACTG TTCAGAGACT G CCCAGCCCT     840

AGGGCACTGT GCCACCCTCA TTCCTCCAGA GCTTGACCCC TGGACATTTG C ACTGACTTT     900

ATCCAGACCA AAGAGCTGCC TCTTGGTGGC AGTATTCCCA CAGAGGGGTA G CTGGGATCA     960

TGCTAGTCAC TTCCTGCCCC CAGGCACCGT GCCAAAGACT GGATGCCCCC T ACTCCTCAG    1020

GGGACTGTCC AGGGCGCCCA GTGGTAGTGA GGGAGAGTGT CTCTGTTCTT T TGCTCAGCC    1080

TGCTGGGCCC TTTGTGTTTG AGGATGCTTA ATGATTCCAG CCTCTCACTG T GCCTTATGC    1140

ATTAAAATTT CTTTGTTACG AGCAAAAAAA AA                                  1172
```

(2) INFORMATION FOR SEQ ID NO: 9:

(i) SEQUENCE CHARACTERISTICS:
        (A) LENGTH: 1469 base pairs
        (B) TYPE: nucleic acid
        (C) STRANDEDNESS: single
        (D) TOPOLOGY: linear (vii) IMMEDIATE SOURCE:
        (A) LIBRARY: COLNNOT05
        (B) CLONE: 775601

(xi) SEQUENCE DESCRIPTION: SEQ ID NO: 9 :

```
GAGCCAGGCG AGTGCCGCGG CGGAGCGCGG TGNCCTTTGC GCGCGGNANG G GGCCTGGGC      60

TTCGGCTCCC TCCGGTTCCC TGGAAGCGGG CCCNGACCAG NCGGAGCAGC A GCAGAGGCG     120

GAGNTCCAGC NGTCTCTCTC CTCCCCCTCA GCCTGAGCCG GGGGAANCAG N CGCCCGGGT     180

GTCTGGAGGG GGGGGGGTCC GCTGCCCGAG AATGGGAATT CTCCTTCACTA G AATATGGAG    240
```

-continued

```
ACTGTTCAAT CACCAGGGCC CGCGAGGCTC GTCGCAGACG AACGCGGCGG C GATGTCCGC      300

GAGCCTAGAG CACAAAGTTA TCATTGTTGG GCTGGATAAT GCAGGGAAAA C TACCATTCT      360

TTACCAATTT TCTATGAACG AAGTTGTACA TACATCTCCT ACAATAGGAG G TAATGTAGA      420

AGAGATAGCG ATTAATAATA CACGTTTCCT AATGTGGGAT ATTGGTGGCC A AGAATCTCT      480

TCGTTCTTCC TGGAACACTT ACTATACTAA CACAGAGTTG GTAATAGTTG T TGTGGACAG      540

TACAGACAGA GAGAGGATTT CTGTAACTAG AGAAGAACTC TATAAAATGT T AGCGCATGA      600

GGACCCAAGA AAAGCTGGAT TGCTGATTTT TGCTAATAAA CAAGATGTTA A AGAATGCAT      660

GACTGTAGCA GAAATCTCCC AGTTTTTGAA GCTAACTTCT ATTAAAGATC A CCAGTGGCA      720

TATCCAGGCA TGCTGTGCTC TAACTGGCGA GGGATTGTGC CAAGGACTTG A ATGGATGAT      780

GTCACGACTT AAGATTAGAT GATCTCTACT GACCTCTACT CATAGATTTT G TATAAATGA      840

AGTGCTGGAC TTTACCTGAA AGCTGCAAAA ATTAATGGTT TAGATATATT T ATAATAAAC      900

TGATTTAAAC TTTTTCTATA AGAAGAAAAA TTAAGACCAC TTATTTGAAA A CAAAGATGA      960

AGTCTCACCT TCCAGTTTGC TTTCTCATTA GTTTTTTCCA AAGTAAGTTA T TGAAGCTGT     1020

GATTGACATT TTTCTCATAA TGAATCCTCT CAGGACATTG TGTAGCCTAT G GTAAGTACA     1080

AAGGGAGAGG AAGACATTTT GAATTTTAAG AGCTTTATTA TCAGTTTAAC C CTCCCTAGT     1140

TGAATGTTAT TTTCTTCTTG TTCCATTAAG TCAGAATACA AATCAGCACA G ATATTCGAA     1200

TGTTTCCAAT ATTTTAAAAT GTAATGTTAC TTATGAAAAG TATTTTGCTT A AGGTTGTGT     1260

GTGTATTGTG TATATACCTC AAGTTCAAGT TAATGGCATT GATTTATGTT C CAGACAAAA     1320

ATAACACAAA TAATAATATC CTTCGTTATA ACCACAATGA GATAAGTATT G GCATTAGTG     1380

TTCAGTGCCA TTTTATACTT TCTCTCTGTG TTCTCTGTAT TGTACTAACC A ACCTCCCAA     1440

ATCGCTGAGC TGCTTGTTTA AAAAAAAA                                         1469
```

(2) INFORMATION FOR SEQ ID NO: 10:

(i) SEQUENCE CHARACTERISTICS:
        (A) LENGTH: 875 base pairs
        (B) TYPE: nucleic acid
        (C) STRANDEDNESS: single
        (D) TOPOLOGY: linear (vii) IMMEDIATE SOURCE:
        (A) LIBRARY: UCMCL5T01
        (B) CLONE: 1528559

(xi) SEQUENCE DESCRIPTION: SEQ ID NO: 10 :

```
CGGGCACGCC AGGCGCCGTT GCCACCCGGG ATGGCGAGGC CCCCGAGCGC T CCCCGCCCT       60

GCAGTCCGAG CTACGACCTC ACGGGCAAGG TGATGCTTCT GGGAGACACA G GCGTCGGCA      120

AAACATGTTT CCTGATCCAA TTCAAAGACG GGGCCTTCCT GTCCGGAACC T TCATAGCCA      180

CCGTCGGCAT AGACTTCAGG AACAAGGTGG TGACTGTGGA TGGCGTGAGA G TGAAGCTGC      240

AGATCTGGGA CACCGCTGGG CAGGAACGGT TCCGAAGCGT CACCCATGCT T ATTACAGAG      300

ATGCTCAGGC CTTGCTTCTG CTGTATGACA TCACCAACAA ATCTTCTTTC G ACAACATCA      360

GGGCCTGGCT CACTGAGATT CATGAGTATG CCCAGAGGGA CGTGGTGATC A TGCTGCTAG      420

GCAACAAGGC GGATATGAGC AGCGAAAGAG TGATCCGTTC CGAAGACGGA G AGACCTTGG      480

CCAGGGAGTA CGGTGTTCCC TTCCTGGAGA CCAGCGCCAA GACTGGCATG A ATGTGGAGT      540

TAGCCTTTCT GGCCATCGCC AAGGAACTGA AATACCGGGC CGGGCATCAG G CGGATGAGC      600

CCAGCTTCCA GATCCGAGAC TATGTAGAGT CCCAGAAGAA GCGCTCCAGC T GCTGCTCCT      660
```

-continued

```
TCATGTGAAT CCCAGGGGGC AGAGAGGAGG CTCTGGAGGC ACACAGGATG C AGCCTTCCC        720

CCTCCCAGGC CTGGCTTATT CCAAGAGGCT GAGCCAATGG GGAGAAAGAT G GAGGACTCA        780

CTGCACAGCC GCTTCCTAGC AGGGAGCTAT ACTCCAACTC CTACTTGAGT T CCTGCGGTC        840

TCCCCGCATC CACAGGGAGG GTAAAACACT TAGGG                                    875
```

(2) INFORMATION FOR SEQ ID NO:   11:

(i) SEQUENCE CHARACTERISTICS:
        (A) LENGTH: 1533 base pairs
        (B) TYPE: nucleic acid
        (C) STRANDEDNESS: single
        (D) TOPOLOGY: linear (vii) IMMEDIATE SOURCE:
        (A) LIBRARY: PROSTUT08
        (B) CLONE: 1651593

(xi) SEQUENCE DESCRIPTION: SEQ ID NO: 11 :

```
CTGGCATCGC CAGATGCTGC GCACAGTCTC CGATTCCCCA TCACCAATTC G GCTGGGGTC         60

TGCGCGGGCC CGGCCCCCAC CAGACGGGAC TCCCCGCCCC CAATTGGCGG C CGAAGAGTC        120

TCCTCGCCCC AGAGTCATCT TCGGGACGCC CAGGGCCCGG GTGATTTTGG G CTCGCCGCG        180

GCCCCGGGTG ATTGTTTCAT CTCCGTGGCC CGCGGTGGTC GTAGCGTCTC C GAGACCGCG        240

GACTCCCGTA GGTCCCCGTG GCCCCGAGTT GTAGTCGGGA CACCCCGGCC G CGGGTGATC        300

GTCGGGTCTC CACGCGCCCG GGTCGCTGAC GCGGATCCGG CCTCGGCGCC T TCTCAGGGC        360

GCCCTGCAAG GCCGCAGGCA GGATGAACAT TCTGGCACCC GTGCGGAGGG A TCGCGTCCT        420

GGCGGAGCTG CCCCAGTGCC TGAGGAAGGA GGCCGCTTTG CACGGGCACA A AGACTTCCA        480

CCCCCGCGTC ACCTGCGCCT GCCAGGAGCA CCGGACAGGC ACCGTGGGCA G ATTTAAGAT        540

CTCCAAGGTC ATTGTGGTGG GGGACCTGTC GGTGGGGAAG ACTTGCCTCA T TAATAGGTT        600

CTGCAAAGAC ACCTTTGATA AGAATTACAA GGCCACCATT GGAGTGGACT T CGAGATGGA        660

ACGATTTGAG GTGCTGGGCA TTCCCTTCAG TTTGCAGCTT TGGGATACCG C TGGGCAGGA        720

GAGGTTCAAA TGCATTGCAT CAACCTACTA TAGAGGAGCT CAAGCCATCA T CATTGTCTT        780

CAACCTGAAT GATGTGGCAT CTCTGGAACA TACCAAGCAG TGGCTGGCCG A TGCCCTGAA        840

GGAGAATGAC CCTTCCAGTG TGCTTCTCTT CCTTGTAGGT TCCAAGAAGG A TCTGAGTAC        900

CCCTGCTCAG TATGCGCTGA TGGAGAAAGA CGCCCTCCAG GTGGCCCAGG A GATGAAGGC        960

TGAGTACTGG GCAGTCTCAT CTCTCACTGG TGAGAATGTC CGAGAATTCT T CTTCCGTGT       1020

GGCAGCACTG ACCTTTGAGG CCAATGTGCT GGCTGAGCTG GAGAAATCGG G GCTCGACG        1080

CATTGGGGAT GTTGTCCGCA TCAACAGTGA TGACAGCAAC CTCTACCTAA C TGCCAGCAA       1140

GAAGAAGCCC ACATGTTGCC CATGAGGGCT GAGGAGACTG TTCAGAGACT G CCCAGCCCT       1200

AGGGCACTGT GCCACCCTCA TTCCTCCAGA GCTTGACCCC TGGACATTTG C ACTGACTTT       1260

ATCCAGACCA AAGAGCTGCC TCTTGGTGGC AGTATTCCCA CAGAGGGGTA G CTGGGATCA       1320

TGCTAGTCAC TTCCTGCCCC CAGGCACCGT GCCAAAGACT GGATGCCCCC T ACTCCTCAG       1380

GGGACTGTCC AGGGCGCCCA GTGGTAGTGA GGGAGAGTGT CTCTGTTCTT T TGCTCAGCC       1440

TGCTGGGCCC TTTGTGTTTG AGGATGCTTA ATGATTCCAG CCTCTCACTG T GCCTTATGC       1500

ATTAAAATTT CTTTGTTACG AGCAAAAAAA AAA                                    1533
```

(2) INFORMATION FOR SEQ ID NO:   12:

(i) SEQUENCE CHARACTERISTICS:

(A) LENGTH: 1173 base pairs
        (B) TYPE: nucleic acid
        (C) STRANDEDNESS: single
        (D) TOPOLOGY: linear (vii) IMMEDIATE SOURCE:
        (A) LIBRARY: BLADNOT05
        (B) CLONE: 1673056

(xi) SEQUENCE DESCRIPTION: SEQ ID NO: 12 :

```
ATATTTTAGA AATCTAGCAT TTTAGAATTC TTGGGCATTT TTAAATACAG G TGAATATTT         60

GAATTTGGTT TGACACAAAA TACAGAATGG ATGAAGCATG CAGATGTTTG G CGTGTGCCC        120

CGAAGCACCC TCTACTCTGT CCTCTGCACC CACCCTTTGC GCCTCTGCGT C AGCCACAGC        180

TGCCCCGGGA GCGAGTTCTC CTGAGGCCCT GGCTGTGCTG ACTCTAGGGC A GCGTGAGGG        240

TGGTTGTCAG CTGTGAAGGT GCCACTTACA CACTAAGTCC TCCTTCCTTG T GGAGGGAAG        300

GGCTCAAGTA GCAAATATTG GAGCCCCGC TTGGTGCTGG GAGCTGTGAC A GGCAGCTCC         360

TGAAGAAGCA GTTTAATTGG AACCAGTGAC CATCTAAAAC TGTTTGTACT C TAAACCAGA        420

TTTTACAGAA ATATTGGAAT CATACCTTTA TACTTGATTT TTTCATTTTA G ATAGTTAGG        480

CGTAAAGGAA GCCTCCTGAG GGTCTGGTCT GATCCTCCTG ATCCTTGAAG A GCTTCCAGC        540

ATCATTCTCC CTTCATGCTC CCCATTTTCA TAAGTAACTG GTGGCTTGAC A TGCTGGGTT        600

TGGTTTGGGA GCCCTCTGAC AAACTGAAAG GGTGGATCAG GAAGCGTCTG A CCACACCAC        660

TGGTAGCTGG ACAAGAAGAT TATGACAGAT TACGCACCCT ATCCTATCCG C AAACAGTTG        720

GAGAAACGTA CGGTAAGGAT ATAACCTCCC GGGGCAAAGA CATGCCGATT G CCGATGTGT        780

TCTTAATTTG CTTTTCCCTT GTGAGTCCTG CATCATTTGA AAATGTCCGT G CAAAGTGGT        840

ATCCTGAGGT GCGGCACCAC TGTCCCAACA CTCCCATCAT CCTAGTGGGA A CTAAACTTG        900

ATCTTAGGGA TGATAAAGAC ACGATCGAGA AACTGAAGGA GAAGAAGCTG A CTCCCATCA        960

CCTATCCGCA GGGTCTAGCC ATGGCTAAGG AGATTGGTGC TGTAAAATAC C TGGAGTGCT       1020

CGGCGCTCAC ACAGCGAGGC CTCAAGACAG TGTTTGACGA AGCGATCCGA G CAGTCATCT       1080

GCCCGCCTCC CGTGAAGAAG AGGAAGAGAA AATGCCTGAT GTTGTAAATG T CTCAGCCCC       1140

TCGTTCTTGT CCTGCCCTTG GACCTTTTGC GTC                                    1173
```

(2) INFORMATION FOR SEQ ID NO:    13:

(i) SEQUENCE CHARACTERISTICS:
        (A) LENGTH: 803 base pairs
        (B) TYPE: nucleic acid
        (C) STRANDEDNESS: single
        (D) TOPOLOGY: linear (vii) IMMEDIATE SOURCE:
        (A) LIBRARY: OVARTUT10
        (B) CLONE: 2703745

(xi) SEQUENCE DESCRIPTION: SEQ ID NO: 13 :

```
CAGCACTCTC GCCCCAGACA GACCTGGTAG ATGACAACGC TAAATCTTTT A GCTCACAGA         60

AGGCTTACAA GATTGTACTT GCTGGGGACG CTGCAGTGGG GAAGTCTAGT T TCCTCATGG        120

AGACTTTGCA AGAATGAATT TCGAGAAAAT ATAAGCGCCA CCCTGGGAGT T GATTTCCAA        180

ATGAAAACCC TCATTGTGGA TGGAGAACGA ACAGTTCTGC AGCTCTGGGA T ACAGCTGGT        240

CAGGAGAGAT TCAGAAGTAT TGCCAAGTCT TACTTCAGAA AGGCAGATGG T GTTTTGCTG        300

CTGTATGATG TTACATGTGA GAAAAGCTTT CTTAACATAC GAGAATGGGT A GATATGATT        360

GAGGATGCAG CCCATGAGAC TGTTCCCATT ATGCTGGTAG GAAACAAGGC T GACATTCGT        420
```

-continued

```
GACACTGCTG CTACAGAGGG ACAAAAATGT GTCCCAGGGC ACTTTGGAGA G AAACTGGCC       480

ATGACGTATG GGGCATTATT CTGTGAAACA AGTGCCAAAG ATGGTTCTAA C ATAGTGGAG       540

GCTGTTCTGC ACCTTGCTCG AGAAGTGAAA AAGAGAACTG ACAAGGATGA C AGCAGATCC       600

ATTACCAATC TAACCGGGAC CAATTCCAAA AAGTCACCAC AGATGAAGAA T TGTTGCAAT       660

GGCTAAATCC CAAACATCCT TGGCCTGTGA AGTCTTCATT TCCAGAATAC T GAATTTGTG       720

TGACTTATTT GGCTCTTAAC AGAGTGGCAC ATCCTACTGA CACTGTCCTA T GGAGAGTTA       780

CAGTGCAGGA AACCTGAACC CAG                                               803

(2) INFORMATION FOR SEQ ID NO:    14:

(i) SEQUENCE CHARACTERISTICS:
        (A) LENGTH: 890 base pairs
        (B) TYPE: nucleic acid
        (C) STRANDEDNESS: single
        (D) TOPOLOGY: linear (vii) IMMEDIATE SOURCE:
        (A) LIBRARY: PENCNOT06
        (B) CLONE: 3440519

(xi) SEQUENCE DESCRIPTION: SEQ ID NO: 14 :

GTCGCCATGT CCTCGGTGTT TGGAAAACCC CGCGCGGGCA GCGGGCCTCA G AGCGCGCCC        60

CTCGAGGTCA ACCTGGCCAT CCTGGGGCGC CGCGGGGCTG GCAAGTCTGC C CTGACCGTG       120

AAGTTTCTGA CCAAGAGGTT TATCAGTGAA TATGACCCCA ACTTGGAGGA C ACCTACAGC       180

TCCGAGGAGA CTGTGGACCA CCAGCCTGTC CACCTGAGGG TCATGGACAC T GCAGACCTG       240

GACACCCCCA GGAACTGCGA GCGCTACCTG AACTGGGCCC ATGCCTTCCT G GTGGTGTAC       300

AGCGTCGACA GCCGCCAGAG CTTTGATAGC AGCAGCAGCT ACCTGGAGCT G CTTGCCTTG       360

CACGCGAAGG AGACACAGCG CAGCATCCCT GCCCTGCTGC TGGGCAACAA G CTGGACATG       420

GCTCAGTACA GGCAAGTCAC CAAGGCAGAG GGTGTGGCTT TGGCAGGCAG G TTTGGGTGC       480

CTGTTTTTCG AGGTCTCTGC CTGTCTGGAC TTTGAGCACG TGCAGCATGT C TTCCACGAG       540

GCAGTGCGAG AGGCACGGCG GGAGCTGGAG AAGAGCCCCC TGACCCGGCC C CTCTTCATC       600

TCCGAGGAGA GGGCCCTGCC CCACCAGGCC CCGCTCACTG CGCGGCATGG G CTGGCCAGC       660

TGCACCTTCA ACACGCTCTC CACCATCAAC CTGAAGGAGA TGCCCACTGT G GCCCAGGCC       720

AAGCTGGTCA CCGTGAAGTC ATCCCGGGCC CAGAGCAAGC GCAAGGCGCC T ACCCTGACT       780

CTCCTGAAGG GCTTCAAGAT CTTCTGAGGC CCCCTCCCCA GGAAGCCTAG G CTCGGTGGC       840

TGGACAGGAC TGCAGCAGGA CAGGGACTGG CTTCTCACCA CCAGCCTTTC                  890
```